United States Patent
Whiteford (12)

(10) Patent No.: US 6,399,592 B1
(45) Date of Patent: *Jun. 4, 2002

(54) BISHPHOSPHONATE/ESTROGEN SYNERGISTIC THERAPY FOR TREATING AND PREVENTING BONE LOSS

(75) Inventor: Donna T. Whiteford, Brooklyn, NY (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/880,735

(22) Filed: Jun. 23, 1997

Related U.S. Application Data

(63) Continuation of application No. 08/491,846, filed on Jun. 22, 1995, now abandoned, which is a continuation-in-part of application No. PCT/US93/12302, filed on Dec. 17, 1993, application No. 08/880,735, which is a continuation-in-part of application No. 07/996,418, filed on Dec. 23, 1992, now abandoned.

(51) Int. Cl.[7] .......................... A61K 31/56; A61K 31/66
(52) U.S. Cl. ........................................ 514/109; 514/182
(58) Field of Search ................................. 514/167, 182, 514/109

(56) References Cited

U.S. PATENT DOCUMENTS

| | | | |
|---|---|---|---|
| 4,621,077 A | 11/1986 | Rosini et al. | 514/108 |
| 4,876,248 A | 10/1989 | Breliere et al. | 514/108 |
| 4,922,007 A | 5/1990 | Kieczykowski et al. | 562/13 |
| 4,927,814 A | 5/1990 | Gall et al. | 514/108 |
| 4,970,335 A | 11/1990 | Isomura et al. | 562/13 |
| 5,019,651 A | 5/1991 | Kieczykowski | 562/13 |
| 5,773,477 A | 6/1998 | MacLean et al. | 514/648 |

FOREIGN PATENT DOCUMENTS

| | | |
|---|---|---|
| EP | 496 520 | 1/1992 |
| WO | WO 92/05187 | 9/1991 |
| WO | WO 92/14474 | 9/1992 |

OTHER PUBLICATIONS

Bone, Henry G., et al., "Alendronate and Estrogen Effects in Postmenopausal Women with Low Bone Mineral Density", J. Clinical Endocrinology & Metabolism, vol. 85, No. 2, pp 720–726, 2000.

Lindsay, Robert, et al., "Addition of Alendronate to Ongoing Hormone Replacement Therapy in the Treatment of Osteoporosis: A Randomized, Controlled Clinical Trial", J. Clinical Endocrinology & Metabolism, vol. 84, No. 9, pp. 3076–3081, 2000.

Fleisch, Bisphosphonates in Bone Disease (2nd ed. 1995), p. 35.

British Med. Bull. 46 (1), pp. 94–112 (1990).

J. Org. Chem., 32, pp. 4111–4114 (1967).

Abstr. 732 and 732, ASBMR Mtg., Minn. (Fall 1992).

Ciminera, N., et al., Ann. Ostet. Ginecol. Med. Perinat., vol. 113, No. 5, pp. 232–237, 1992.

*Primary Examiner*—Theodore J. Criares
(74) *Attorney, Agent, or Firm*—Nicole M. Wallinger; Mark R. Daniel

(57) ABSTRACT

Disclosed is a combination therapy for treating and for preventing bone loss by the use of estrogen and a bisphosphonate selected from: alendronate, clodronate, tiludronate, YM175, BM 210995, or mixture thereof. Also described is a pharmaceutical composition of the above for carrying out the therapeutic method.

19 Claims, No Drawings

BISHPHOSPHONATE/ESTROGEN SYNERGISTIC THERAPY FOR TREATING AND PREVENTING BONE LOSS

CROSS REFERENCE TO RELATED APPLICATIONS

This application is a continuation of U.S. Ser. No. 08/491,846, filed Jun. 22, 1995, now abandoned, which was a U.S. continuation-in-part national filing of PCT/US93/12302, filed Dec. 17, 1993, which had published as WO 94/14455 on Jul. 7, 1994, which is a C-I-P from parent U.S. Ser. No. 07/996,418, filed Dec. 23, 1992, now abandoned.

FIELD OF THE INVENTION

The instant invention relates generally to the combination of estrogen and bisphosphonates and their use in bone growth and maturation. Specifically, the invention relates to the use of estrogen and bisphosphonates to inhibit bone resorption and promote net bone formation. This therapeutic combination will result in a decreased rate of bone resorption with either an increase or stabilization of bone mass.

BACKGROUND OF THE INVENTION

The normal bones are living tissues undergoing constant resorption and redeposition of calcium, with the net effect of maintenance of a constant mineral balance. The dual process is commonly called "bone turnover". In normal growing bones, the mineral deposition exceeds the mineral resorption, whereas in certain pathological conditions, bone resorption exceeds bone deposition, for instance due to malignancy or primary hyperparathyroidism, or in osteoporosis. In other pathological conditions the calcium deposition may take place in undesirable amounts and areas leading to e.g. heterotopic calcification, osteoarthritis, kidney or bladder stones, atherosclerosis, and Paget's disease which is a combination of an abnormal high bone resorption followed by an abnormal calcium deposition.

Most of the currently available therapeutic agents for the treatment of osteoporosis, e.g. estrogens, act by reducing bone resorption in the osteoporotic patient. See the review article, British Medical Bulletin 46 (1), p. 94–112 (1990).

Bisphosphonates are also known in the art as bone resorption inhibitors.

Alendronate, 4-amino-1-hydroxybutylidene-1,1-bisphosphonic acid monosodium trihydrate, is described as a composition, method of use and synthesis in U.S. Pat. Nos. 4,621,077 (Gentili); 4,922,007 and 5,019,651 (Merck).

Clodronate, (dichloromethylene)bisphosphonic acid disodium salt (Proctor and Gamble, is described in Belgium Patent 672,205 (1966) and J. Org. Chem 32, 4111 (1967) for its preparation.

Tiludronate, ([(4-chlorophenyl)thiomethylene]-bisphosphonic acid) (Sanofi) is described in U.S. Pat. No. 4,876,248 issued Oct. 24, 1989.

YM 175 ([(cycloheptylamino)methylene]bisphosphonic acid, disodium salt) by Yamanouchi is described in U.S. Pat. No. 4,970,335 issued Nov. 13, 1990.

BM 210995 (1-Hydroxy-3-(methylpentylamino)-propylidene-bisphosphonate) by Boehringer-Mannheim—is described in U.S. Pat. No. 4,927,814 issued May 22, 1990.

A study by Proctor and Gamble (Norwich Eaton Pharmaceuticals) using risendronate, whose chemical name is sodium trihydrogen [1-hydroxy-2-(3-pyridinyl) ethylidene]bisphosphonate, in combination with estrogen showed a positive effect on bone loss in ovaricetomized rats (published in Abstracts 731 and 732 at the Fall 1992 ASBMR meeting in Minnesota.

The article, J. Clin. Invest., Jan. 1992, 89 (1), p. 74–78 by J. Chow et al., describes the effect of estrogen on ovariectomized rats in which bone resorption was suppressed by pamidronate. They concluded that estrogen inhibits bone resorption and also stimulates bone formation.

The article, J. Bone Miner. Res. (USA) 1991, p. 387–394 by T. J. Wronski et al., describes studies in rats with estrogen and the bisphosphonates etidronate and risedronate. The studies showed that etidronate, (1-hydroxyethylidene) bisphosphonic acid, disodium salt, (Proctor and Gamble) has long term adverse effects on bone mineralization.

However, these studies did not suggest the use of other bisphosphonates including alendronate.

There are situations where a female patient is undergoing estrogen therapy for a menopausal or postrnenopausal-related condition, (e.g., vasomotor symptoms, atrophy of the vaginal mucosa, increased cardiovascular risk, etc.) and is also discovered to be suffering from osteoporosis (i.e. rarefaction of bone) or to be at risk for developing osteoporosis.

Although estrogens/hormone replacement therapy (HRT) are known to help prevent the development of osteoporosis, there are instances, which are not at all uncommon, where HRT or a weak estrogen is prescribed at dosages which do not provide adequate protection against osteoporosis. There are also some women who continue to lose bone mass despite treatment with higher estrogen/HRT doses or who have established osteoporosis but fail to increase their bone mass on estrogen/HRT alone.

What is desired in these cases is a therapy to optimally treat both the menopausal and postmenopausal-related conditions and the development of osteoporosis or osteoporosis risk concurrently.

SUMMARY OF THE INVENTION

The present invention discloses a combination method for treating and/or preventing bone loss in a subject by the combination therapy of pharmaceutically effective amounts of estrogen and of a bisphosphonate selected from: alendronate, clodronate, tiludronate, YM 175, BM 210995, or mixture thereof.

Also described is a pharmaceutical composition containing the combination described above in a pharmaceutically acceptable carrier.

DETAILED DESCRIPTION OF THE INVENTION AND PREFERRED EMBODIMENTS

By the term "estrogen" as used herein is meant "17-beta estradiol" and includes those equivalent materials contained in the MERCK INDEX—Eleventh Edition (1989). Estrogens, e.g. estradiol and its steroidal and non-steroidal equivalents which can be used herein include (page numbers taken from the above indicated MERCK INDEX):

| ESTROGEN |
|---|
| Nonsteroidal |
| Benzestrol, 1082 |
| Broparoestrol, 1438 |

-continued

ESTROGEN

Chlorotrianisene, 2173
Dienestrol, 3094
Diethylstilbestrol, 3118
Diethylstilbestrol Dipropionate, 3119
Dimestrol, 3198
Fosfestrol, 4168
Hexestrol, 4621
Methallenestril, 5856
Methestrol, 5888
Tamoxifen, 9019
Steroidal Colpormon, 2485
Conjugated Estrogenic Hormones, 2504
Equilenin, 3581
Equilin, 3582
Estradiol, 3653
Estradiol Benzoate, 3655
Estradiol 17β-Cypionate, 3656
Estriol, 3659
Estrone, 3660
Ethinyl Estradiol, 3689
Mestranol, 5819
Moxestrol, 6203
Mytatrienediol, 6254
Progesterone, 7783
Quinestradiol, 8065
Quinestrol, 8066 and including estrogen/progestin combinations.

By the term "bisphosphonates" as used herein is meant bisphosphonates of the structure:

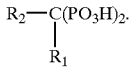

in which $R_1$ is OH or H and $R_2$ is an $C_1$–$C_5$ linear, branched or cyclic alkyl or alkylidene which can be substituted by an terminal amino, substituted amino, e.g. dimethylamino, methylamino, ethylamino, heterocyclic amino, and the like. Also included within the term "bisphosphonates" are the bisphosphonates described above, and those in the U.S. Pat. Nos. 4,732,998; 4,870,063; 5,130,304 to Leo Pharmaceuticals. Excluded from this category is risedronate.

The method can be used to treat subjects in general, including sport, pet, and farm animals, and humans.

The term "inhibition of bone resorption" refers to prevention of bone loss, especially the inhibition of removal of existing bone either from the mineral phase and/or the organic matrix phase, through direct or indirect alteration of osteoclast formation or activity. Thus, the term "inhibitor of bone resorption" as used herein refers to agents that prevent bone loss by the direct or indirect alteration of osteoclast formation or activity.

The term "osteogenically effective" means that amount which effects the turnover of mature bone. As used herein, an osteogenically effective dose is also "pharmaceutically effective."

The term "subject" as used herein refers to a living vertebrate animal such as a mammal or bird in need of treatment, i.e., in need of bone repair or replacement. Such need arises locally in cases of bone fracture, non-union, defect, prosthesis implantation, and the like. Such need also arises in cases of systemic bone disease, as in osteoporosis, osteoarthritis, Paget's disease, osteomalacia, multiple myeloma and other forms of cancer, steroid therapy, and age-related loss of bone mass. Particularly preferred is a human female subject.

The term "treatment" or "treating" as used herein shall mean (1) providing a subject with an amount of a substance sufficient to act prophylactically to prevent the development of a weakened and/or unhealthy state; and/or (2) providing a subject with a sufficient amount of a substance so as to alleviate or eliminate a disease state and/or the symptoms of a disease state, and a weakened and/or unhealthy state.

Method of Use

Drugs which prevent bone loss and/or add back lost bone may be evaluated in the ovariectomized rat. This animal model is well established in the art (see, for example, Wronski, et al. (1985) Calcif. Tissue Int. 37:324–328; Kimmel, et al. (1990) Calcif. Tissue Int. 46:101–110; and Durbridge, et al. (1990) Calcif. Tissue Int 47:383–387; these references are hereby incorporated in their entirety). Wronski, et al. ((1985) Calcif. Tissue Int. 43:179–183)) describe the association of bone loss and bone turnover in the ovariectomized rat.

Pharmaceutical formulations of the invention which include a bone growth factor and/or an inhibitor of bone resorption for administration will generally include an osteogenically effective amount of the bone growth factor to promote bone growth, in addition to a pharnaceutically acceptable excipient. Suitable excipients include most carriers approved for parenteral administration, including water, saline, Ringer's solution, Hank's solution, and solutions of glucose, lactose, dextrose, ethanol, glycerol, albumin, and the like. These compositions may optionally include stabilizers, antioxidants, antimicrobials, preservatives, buffering agents, surfactants, and other accessory additives. The inhibitor of bone resorption may also be delivered in a sustained release form from a suitable carrier.

A presently preferred vehicle comprises about 1 mg/ml serum albumin (species-specific) in phosphate-buffered saline (PBS) or isotonic citrate buffer. A thorough discussion of suitable vehicles for parenteral administration may be found in E. W. Martin. "Remington's Pharmaceutical Sciences" (Mack Pub. Co., current edition sections relating to the excipient vehicles and formulating being incorporated herein by reference to disclose such). Such formulations are generally known to those skilled in the art and are administered systemically to provide systemic treatment.

The estrogen and bisphosphonate may be administered sequentially or concurrently in separate dosages or as a single composition to the subject. If administered sequentially, the period between the administration of the estrogen and bisphosphonate will typically be one week to one year, and optimally, one week to six months.

If the estrogen and bisphosphonate are administered as a single composition, the molar ratio of the estrogen and bisphosphonate will be about 50:1 to 1:50, preferably, 5:1 to 1:5. The optimal ratio is expected to vary from compound to compound. Furthermore, if administered as a single composition the estrogen and bisphosphonate may be separate components of the composition, or they may be conjugated to each other. Methods for conjugating bone growth factors to other agents are described above.

The precise dosage necessary will vary with the age, size, sex and condition of the subject, the nature and severity of the disorder to be treated, and the like; thus, a precise effective amount cannot be specified in advance and will be determined by the caregiver. However, appropriate amounts may be determined by routine experimentation with animal models, as described below. In general terms, an effective dose of estrogen for systemic treatment will range from about 0.001 µg/kg to about 50 µg/kg of body weight and preferably about 30 µg/kg of body weight. An effective dose for biphosphonate is about 1.5 to 3000 μg/kg of body weight and preferably about 10 μg/kg to about 200 μg/kg of body weight.

Effective doses for local administration would be about 0.001 μg to 1 mg per application site.

The methods and compositions of the invention are useful for treating bone fractures defects and disorders which result in weakened bones such as osteoporosis, osteoarthritis, Paget's disease, osteohalisteresis, osteomalacia, bone loss resulting from multiple myeloma other forms of cancer, bone loss resulting from side effects of other medical treatment (such as steroids), and age-related loss of bone mass.

In accordance with one method of use the estrogen and bisphosphonate may be administered systemically either orally and/or parenterally, including subcutaneous or intravenous injection. Additionally, the estrogen and bisphosphonate make be delivered in a slow release form from a suitable carrier.

In accordance with another method of use, the estrogen may be administered locally to a specific area in need of bone growth or repair, with either the concomitant administration of the bisphosphonate at the site, or the administration of the bisphosphonate in a separate vehicle, or the inhibitor of bone resorption may be provided locally with the administration of the estrogen in a separate vehicle. Thus, the estrogen and/or bisphosphonate may be implanted directly at the site to be treated, for example, by injection or surgical implantation in a sustained-release carrier. Suitable carriers include hydrogels, controlled—or sustained-release devices (e.g., an Alzet® minipump), polylactic acid, and collagen matrices. Presently preferred carriers are formulations of atelopeptide collagen containing particulate calcium phosphate mineral components, such combinations of homologous or xenographic fibrillar atelopeptide collagen (for example Zyderm® Collagen Implant, available from Collagen Corporation, Palo Alto, Calif.) with hydroxapatitetricalcium phosphate (HA-TCP, available from Zimmer, Inc., Warsaw, Ind.). It is presently preferred to administer implant compositions containing and/or an bisphosphonate in a collagen/mineral mixture implant.

Estrogen and/or an bisphosphonate delivered in sustained-release vehicles is also particularly useful for improving implant fixation, for example for improving in growth of new bone into a metal prosthesis in joint reconstruction and dental or orthopedic implants. Alternatively, the estrogen may be delivered in the implant, with the bisphosphonate delivered in a separate vehicle, and vice-versa.

Dental and orthopedic implants can be coated with estrogen in combination with an bisphosphonate to enhance attachment of the implant device to the bone. Alternatively, the estrogen can be used to coat the implant, and the bisphosphonate can be administered concomitantly or sequentially in a separate vehicle, and vice-versa.

In general, implant devices may be coated with a estrogen and/or an bisphosphonate as follows. The estrogen and the bisphosphonate if desired is dissolved at a concentration in the range of 0.01 μ/ml to 200 mg/ml in phosphate-buffered saline (PBS) containing 2 mg/ml serum albumin. The porous end of an implant is dipped in the solution and is airdried (or lyophilized) or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing the estrogen (and the bisphosphonate, if desired) is mixed with collagen gel or human collagen (e.g. Zyderm® Collagen Implant, Collagen Corp., Palo alto, Calif.) to a final collagen concentration of 2 mg/ml to 100 mg/ml to form a paste or gel, which is then used to coat the porous end of the implant device. The coated implant device is placed into the bony site immediately or is airdried and rehydrate with PBS prior to implanting, with the objective of maximizing new bone formation into the implant while minimizing the ingrowth of soft tissue into the implant site.

The pharmaceutical compositions according to the present invention containing, e.g., both alendronate and estradiol, may be prepared for use in the form of capsules or tablets or in solution for oral administration or for systemic use. The compositions are advantageously prepared together with inert carriers such as sugars (saccharose, glucose, lactose), starch and derivatives, cellulose and derivatives, gums, fatty acids and their salts, polyalcohols, talc, aromatic esters.

Some typical pharmaceutical formulations containing 4-amino-1-hydroxybutane-1, 1-diphosphonic acid monosodium salt trihydrate are shown here below:

TABLE

|  | 1 | | 2 | |
|---|---|---|---|---|
| OPERCOLATED CAPSULES | | | | |
| 4-amino-1-hydroxybutan-1,1-biphosphonicacid, sodium salt trihydrate | mg | 6.5 | mg | 2.5 |
| Estradiol | | 3.0 | | 2.0 |
| Lactose | | 110.0 | | 110.0 |
| Avucek Ph101 | | 80.0 | | 80.0 |
| Aldisol/NF Type A | | 2.0 | | 2.0 |
| Magnesium Stearate | | 1.0 | | 1.0 |
| Total Weight | | 202.5 | | 197.5 |
| EFFERVESCENT GRANULATES | | | | |
| 4-amino-1-hydroxybutan-1,1-biphosphonic acid | mg | 5.0 | mg | 10.0 |
| Estradiol | | 3.0 | | 3.0 |
| Anhydrous Sodium Carbonate | | 12.0 | | 12.0 |
| Sodium Bicarbonate | | 63.0 | | 63.0 |
| Anhydrous Citric Acid | | 110.0 | | 110.0 |
| Sodium Saccharinate | | 5.0 | | 5.0 |
| Saccharose | | 493.0 | | 493.0 |
| Dehydrated Lemon Juice | | 55.0 | | 55.0 |
| Natural Essence of Lemon | | 2.0 | | 2.0 |
| Total Weight | | 748 | | 753 |
| FORMULATIONS SUITABLE FOR INJECTION | | | | |
| 4-amino-1-hydroxybutan-1,1-biphosphonic acid | mg | 0.5 | mg | 1.00 |
| Estradiol | | 0.42 | | 0.84 |
| Sodium Hydroxide | | 0.25 | | 0.25 |
| Sodium Chloride | | 8.40 | | 16.30 |
| Purified Water q h | ml | 1.0 | ml | 12.0 |

What is claimed is:

1. A method for treating and/or preventing bone loss in a subject in need thereof, comprising administering synergistically effective amounts of estrogen and alendronate and the pharmaceutically acceptable salts and mixtures thereof.

2. The method of claim 1 wherein the subject is human.

3. The method of claim 1 wherein the estrogen and alendronate are administered sequentially.

4. The method of claim 1 wherein the estrogen and alendronate are administered concurrently.

5. The method of claim 1 wherein the bone loss is osteoporosis-related.

6. The method of claim 1 wherein the bone loss is due to disuse.

7. The method of claim 1 wherein the bone loss is age-related.

8. The method of claim 1 wherein the bone loss is related to steroid therapy.

9. The method of claim 1 wherein the bone loss is rheumatoid-related.

10. The method of claim 1 wherein the bone loss is related to Paget's disease.

11. The method of claim 1 wherein the bone loss is related to cancer.

12. The method of claim 11 wherein the cancer is multiple myeloma.

13. A composition for inducing net bone formation in a subject in need thereof comprising synergistically effective amounts of estrogen and alendronate and the pharmaceutically acceptable salts and mixtures thereof.

14. The composition of claim 13 wherein the molar ratio of estrogen to alendronate is 50:1 to 1:50.

15. The composition of claim 13 wherein the molar ratio of estrogen to alendronate is 5:1 to 1:5.

16. The composition of claim 13 wherein the estrogen is conjugated to the alendronate.

17. The composition of claim 13 further comprising a sustained-release vehicle.

18. A method for treating, and/or preventing bone loss in a subject in need thereof comprising administering synergistically effective amounts of estradiol and alendronate and the pharmaceutically acceptable salts and mixtures thereof.

19. A method for promoting net bone formation in a subject in need thereof comprising administering synergistically effective amounts of estradiol and alendronate and the pharmaceutically acceptable salts and mixtures thereof.

* * * * *